(12) United States Patent
Siciliano et al.

(10) Patent No.: US 11,857,749 B2
(45) Date of Patent: Jan. 2, 2024

(54) ADAPTER DEVICE FOR TATTOO MACHINE

(71) Applicant: FK Irons Inc., Doral, FL (US)

(72) Inventors: Gaston Siciliano, Doral, FL (US);
Lester Perez, Doral, FL (US);
Fernando Diaz, Doral, FL (US);
Adriano Mendoza, Doral, FL (US);
Juan Martino, Doral, FL (US);
Roberto Hernandez, Doral, FL (US)

(73) Assignee: FK Irons Inc., Doral, FL (US)

( * ) Notice: Subject to any disclaimer, the term of this patent is extended or adjusted under 35 U.S.C. 154(b) by 0 days.

(21) Appl. No.: 17/954,241

(22) Filed: Sep. 27, 2022

(65) Prior Publication Data
US 2023/0012727 A1 Jan. 19, 2023

Related U.S. Application Data

(63) Continuation of application No. 17/670,282, filed on Feb. 11, 2022.
(Continued)

(51) Int. Cl.
A61M 37/00 (2006.01)
H01R 13/625 (2006.01)
H01R 31/06 (2006.01)

(52) U.S. Cl.
CPC ........ A61M 37/0084 (2013.01); H01R 13/625 (2013.01); H01R 31/06 (2013.01); A61M 2205/8206 (2013.01)

(58) Field of Classification Search
CPC .......... A61M 37/0015; A61M 37/0076; A61M 37/0084; A61M 2205/8206;
(Continued)

(56) References Cited

U.S. PATENT DOCUMENTS

| 2,588,623 | A | 3/1952 | Eliscu |
| D226,829 | S | 5/1973 | Staub |

(Continued)

FOREIGN PATENT DOCUMENTS

| CN | 102469867 | 5/2012 |
| CN | 203790439 | 8/2014 |

(Continued)

OTHER PUBLICATIONS

World Intellectual Property Organization, "International Search Report and Written Opinion," dated Jun. 6, 2022, document of 11 pages.

Primary Examiner — Robert A Lynch
(74) Attorney, Agent, or Firm — Akerman LLP; Peter A. Chiabotti

(57) ABSTRACT

An adapter for use with a tattoo machine is disclosed. The adapter may enable a tattoo machine configured with a wireless battery pack to switch to a wired configuration by removing the wireless battery pack and replacing it with the adapter. One end of the adapter may be affixed to a portion of the tattoo machine so that the adapter may deliver power to the componentry of the tattoo machine to facilitate the operation of the tattoo machine. The other end of the adapter may include a connector for enabling connection of the adapter to a power supply or power source so that power may be delivered from the power supply or power source through the adapter and to the tattoo machine. When the tattoo machine is powered, the motor of the tattoo machine may reciprocate a needle included in a needle cartridge affixed to the tattoo machine.

18 Claims, 15 Drawing Sheets

SECTION A-A

Related U.S. Application Data

(60) Provisional application No. 63/149,051, filed on Feb. 12, 2021.

(58) Field of Classification Search
CPC .. A61M 2205/8237; A61M 2205/8262; H01R 13/625; H01R 31/06; H02J 7/00; H02J 7/0063; A01K 11/005
See application file for complete search history.

(56) References Cited

U.S. PATENT DOCUMENTS

| | | |
|---|---|---|
| D229,869 S | 1/1974 | Staub |
| D241,475 S | 9/1976 | Staub |
| D254,150 S | 2/1980 | Barton |
| D288,359 S | 2/1987 | Hoff |
| 4,647,260 A | 3/1987 | O'Hara |
| D294,388 S | 2/1988 | Hardy |
| D294,519 S | 3/1988 | Hardy |
| 5,032,043 A | 7/1991 | Hollifield |
| 5,279,552 A * | 1/1994 | Magnet ............ A61M 37/0076 604/47 |
| 5,341,704 A | 8/1994 | Klemm |
| 5,380,132 A | 1/1995 | Parks |
| D364,923 S | 12/1995 | Chou |
| 5,586,473 A | 12/1996 | Chou |
| 5,601,387 A | 2/1997 | Sanford |
| D380,046 S | 6/1997 | Domanowski |
| D389,578 S | 1/1998 | Emerson |
| D389,915 S | 1/1998 | Emerson |
| 6,033,421 A | 3/2000 | Theiss et al. |
| D433,752 S | 11/2000 | Saravia |
| D434,149 S | 11/2000 | Mirhashemi |
| D439,337 S | 3/2001 | Jones |
| D440,310 S | 4/2001 | Laks |
| D448,483 S | 9/2001 | Behnke |
| D453,833 S | 2/2002 | Hess |
| 6,345,553 B1 | 2/2002 | Adler et al. |
| D457,955 S | 5/2002 | Bilitz |
| D465,279 S | 11/2002 | Etter |
| 6,505,530 B2 | 1/2003 | Adler |
| D490,152 S | 5/2004 | Myall |
| D493,530 S | 7/2004 | Reschke |
| D493,532 S | 7/2004 | Levaughn |
| 6,772,656 B2 | 8/2004 | Godoy |
| D521,641 S | 5/2006 | Reschke |
| D535,396 S | 1/2007 | Reschke |
| D536,451 S | 2/2007 | Haydu |
| D538,934 S | 3/2007 | Wilkinson |
| D538,936 S | 3/2007 | Bohmel |
| 7,211,097 B2 | 5/2007 | Carrasco |
| 7,225,708 B2 | 6/2007 | Chen |
| D549,325 S | 8/2007 | Schnitzler |
| D549,779 S | 8/2007 | Shimizu |
| D560,803 S | 1/2008 | Tasse |
| 7,335,211 B2 | 2/2008 | Chen |
| 7,337,697 B2 | 3/2008 | Bader |
| D575,343 S | 8/2008 | Cetera |
| D581,530 S | 11/2008 | Thierfelder |
| D582,981 S | 12/2008 | Bhavnani |
| D586,465 S | 2/2009 | Faulkner |
| D597,668 S | 8/2009 | Woodruff |
| D612,051 S | 3/2010 | Ruf |
| D621,042 S | 8/2010 | Ruf |
| D622,000 S | 8/2010 | Kluge |
| 7,810,414 B2 | 10/2010 | Hsu |
| D628,293 S | 11/2010 | Ruf |
| D628,695 S | 12/2010 | Ruf |
| D634,426 S | 3/2011 | Zollers |
| D638,939 S | 5/2011 | Eikhoff |
| D645,965 S | 9/2011 | Muto |
| 8,029,527 B2 | 10/2011 | Lisec |
| D664,657 S | 7/2012 | Vieira |
| D667,554 S | 9/2012 | Casabonne |
| D677,790 S | 3/2013 | Little |
| D679,396 S | 4/2013 | Jan |
| 8,414,531 B2 | 4/2013 | Oginski |
| D691,263 S | 10/2013 | Chen |
| 8,794,109 B2 | 8/2014 | Lee |
| 8,920,379 B2 | 12/2014 | Lee |
| D723,685 S | 3/2015 | Myers |
| 9,050,445 B2 | 6/2015 | Klebs |
| D736,915 S | 8/2015 | Schultz |
| D737,441 S | 8/2015 | Presser |
| D737,972 S | 9/2015 | Chen |
| 9,126,027 B2 | 9/2015 | Lin |
| D743,546 S | 11/2015 | Jayaraj |
| D745,152 S | 12/2015 | Mayer |
| D750,243 S | 2/2016 | Tetzlaff |
| D750,258 S | 2/2016 | Crossley |
| 9,259,561 B2 | 2/2016 | Lee |
| D762,303 S | 7/2016 | Jayaraj |
| 9,393,395 B2 | 7/2016 | Miller |
| D763,443 S | 8/2016 | Chen |
| D765,841 S | 9/2016 | Schuerg |
| D765,842 S | 9/2016 | Schuerg |
| D766,432 S | 9/2016 | Schuerg |
| D779,670 S | 2/2017 | Krystyniak |
| D781,419 S | 3/2017 | Bojanowski |
| D782,041 S | 3/2017 | Pell |
| D782,667 S | 3/2017 | Fuhr |
| D785,795 S | 5/2017 | Amano |
| D791,946 S | 7/2017 | Schwartz |
| D791,947 S | 7/2017 | Chen |
| 9,707,385 B1 | 7/2017 | Chen |
| D794,192 S | 8/2017 | Schuerg |
| D794,193 S | 8/2017 | Schuerg |
| D794,194 S | 8/2017 | Schuerg |
| D803,398 S | 11/2017 | Israni |
| D805,195 S | 12/2017 | Lee |
| D805,196 S | 12/2017 | Lee |
| D805,197 S | 12/2017 | Lee |
| D805,198 S | 12/2017 | Lee |
| D805,640 S | 12/2017 | Lee |
| D815,738 S | 4/2018 | Ye |
| D819,207 S | 5/2018 | Blank |
| D831,208 S | 10/2018 | Benisty |
| D837,371 S | 1/2019 | Zu |
| D837,372 S | 1/2019 | Zu |
| D839,425 S | 1/2019 | Zanata |
| 10,449,346 B2 | 10/2019 | Juan |
| 10,471,246 B1 | 11/2019 | Lipscomb |
| 2005/0055042 A1 | 3/2005 | Carrasco |
| 2006/0020283 A1 | 1/2006 | Lisec |
| 2008/0287978 A1 | 11/2008 | Hickman |
| 2010/0036317 A1 | 2/2010 | Oginski |
| 2010/0241151 A1 | 9/2010 | Rickard |
| 2011/0048174 A1 | 3/2011 | Lin |
| 2011/0288575 A1 | 11/2011 | Colton et al. |
| 2012/0123462 A1 | 5/2012 | Lee |
| 2012/0179134 A1 | 7/2012 | Garitano |
| 2014/0358172 A1 | 12/2014 | Lin |
| 2014/0358173 A1 | 12/2014 | Lin |
| 2015/0202420 A1 | 7/2015 | Miller |
| 2016/0038176 A1 | 2/2016 | Smith |
| 2016/0354592 A1 | 12/2016 | Juan |
| 2017/0014609 A1 | 1/2017 | Spadoni, III |
| 2017/0072177 A1 | 3/2017 | Oscar |
| 2017/0157382 A1 | 6/2017 | Siciliano |
| 2017/0317444 A1 | 11/2017 | Narayanasamy et al. |
| 2018/0043146 A1 | 2/2018 | Vescovi |
| 2018/0056054 A1 * | 3/2018 | Siciliano ........... A61M 37/0076 |
| 2018/0289902 A1 | 10/2018 | Xiang |
| 2018/0360487 A1 | 12/2018 | Algeri |
| 2018/0369553 A1 | 12/2018 | Siciliano |
| 2019/0134371 A1 | 5/2019 | Johansson |
| 2020/0038158 A1 * | 2/2020 | Gagliano ............... G10H 1/348 |
| 2020/0121903 A1 | 4/2020 | Vester |
| 2021/0283389 A1 * | 9/2021 | Xiao ....................... H02K 7/06 |

FOREIGN PATENT DOCUMENTS

| | | |
|---|---|---|
| CN | 208081655 | 11/2018 |
| CN | 111659001 | 9/2020 |

(56) References Cited

FOREIGN PATENT DOCUMENTS

| EP | 2944349 | 11/2015 |
|---|---|---|
| KR | 100973628 | 8/2010 |
| KR | 20150009459 | 1/2015 |
| RU | 2270040 | 2/2006 |
| WO | 2010120111 | 10/2010 |
| WO | 2014202055 | 12/2014 |
| WO | 2015094041 | 6/2015 |
| WO | 2015160370 | 10/2015 |
| WO | 2016159465 | 10/2016 |
| WO | 2017189606 | 11/2017 |

* cited by examiner

SECTION A-A

SECTION B-B

ADAPTER DEVICE FOR TATTOO MACHINE

CROSS REFERENCE TO RELATED APPLICATIONS

This application is a continuation of U.S. patent application Ser. No. 17/670,282, filed Feb. 11, 2022, which claims the benefit of U.S. Provisional Patent Application No. 63/149,051, filed on Feb. 12, 2021, each of which is hereby incorporated by reference in its entirety.

FIELD OF THE INVENTION

The present application relates to tattoo machines, adapter devices, power supplies, power delivery technologies, modular technologies, connector technologies, and, more particularly, to an adapter device for a tattoo machine.

BACKGROUND

In today's society, tattooing has become increasingly popular and ubiquitous. As a result, businesses are increasingly devoting financial resources, training skilled tattoo artists, and developing tattoo-related technologies to meet not only the increased demand from tattoo clients, but also the increasing quality and sanitation requirements that have become associated with tattooing. One of the tools that tattoo artists utilize to make tattoos on the skin of a tattoo recipient is a tattoo machine. Such tattoo machines may include motors, power sources, various controls, and other features to facilitate the reciprocation of needles of needle cartridges coupled to the tattoo machines. The reciprocation action of the needle generated by the tattoo machine enables a tattoo artist to apply the tattoo ink to the skin of a tattoo recipient so that the tattoo may be created. Currently, tattoo machines come in all sorts of shapes, colors, sizes, and functionality. Additionally, tattoo machines may be fitted with various grips, accessories, and other components as well, which may facilitate customization of the tattoo machines. Nevertheless, currently existing tattoo machines and tattoo machine accessories still do not provide all of the functionality, ergonomics, and/or features desired by tattoo artists.

As a result, there remains room for substantial enhancements to existing tattoo machine technologies and accessories to meet tattoo artists' needs. While currently existing tattoo machines and accessories provide for various benefits, such technologies still come with various drawbacks. For example, currently existing tattoo machines and accessories are often bulky, unwieldy, and/or difficult to operate. Additionally, current tattoo machines are often fixed in configuration and contribute to tattoo artist fatigue. Furthermore, currently existing tattoo machines have limited options for providing power to the tattoo machines. Based on the foregoing, current tattoo machines and accessories may be improved and enhanced so as to provide for improved modularity, more optimal tattoo machine and accessory combinations, and improved power delivery capabilities. Such enhancements and improvements to methodologies and technologies may provide for increased tattoo artist productivity, enhanced tattoo-making abilities, and enhanced functionality.

SUMMARY

An adapter device for a tattoo machine and accompanying methods for utilizing the adapter device with a tattoo machine are disclosed. In particular, the adapter device enables a tattoo machine to switch from a fully wireless or other configuration to a wired configuration on the fly, such as by removing a wireless battery pack from the tattoo machine and replacing the wireless battery pack with the adapter described in the present disclosure. In certain embodiments, the adapter may be fitted with a connector, such as, but not limited to, a RCA connector that may couple with a power cable that may be utilized to deliver power to the tattoo machine when the tattoo machine is connected to the adapter and the coupled power cable is connected to a power supply supplying the power. The power supply may be any device may connect to a power source, such as a wall socket or other power source, and which may be utilized to deliver power to the tattoo machine via the adapter. For example, the power supply may be a traditional power supply device, a wired or wireless footswitch for controlling the tattoo machine, any other device for controlling the tattoo machine, a programmable power supply, a capacitive power supply, a direct current power supply, an AC-DC power supply, any other power supply, or a combination thereof. In certain embodiments, the adapter may include a female RCA connector attached on one end of the adapter, and, on the opposite end (or other desired location), the adapter may include a printed circuit board with custom designed plating that is configured to make contact with pins on a motor assembly of the tattoo machine so that power may be transferred to the tattoo machine via the adapter. An internal circuit of the printed circuit board may be configured to ensure that the power delivered to the motor of the tattoo machine via the power cable attached to the female RCA connector always has the correct polarity regardless of the input polarity.

In one embodiment, a machine including a tattoo machine portion and an adapter is provided. The tattoo machine portion of the machine may include a receptacle for receiving and connecting to the adapter, and a motor for power and enabling the tattoo machine to operate. In certain embodiments, the adapter may include a first portion configured to connect to the receptacle of the tattoo machine portion, and a second portion including a connector to connect to a power cable for delivering power to the motor of the tattoo machine portion when the first portion of the adapter is connected to the receptacle of the tattoo machine portion. In order to connect the first portion of the adapter to the receptacle of the tattoo machine portion, the first portion may include one or more extruded features that may be inserted axially into the receptacle of the tattoo machine portion. Once inserted, the first portion of the adapter (and the adapter itself) may be twisted in a direction (e.g. clockwise) until at least one of the extruded features contacts a ledge of the receptacle of the tattoo machine portion. When the at least one of the extruded features contacts the ledge of the receptacle of the tattoo machine portion, an o-ring (or other similar component) assembled to the adapter may be squeezed between the adapter and a body of the tattoo machine portion, thereby generating a pulling force on the plurality of extruded features and locking the adapter in place with the receptacle of the tattoo machine portion. When the adapter is locked into place with the receptacle, custom-designed plating of a printed circuit board of the adapter may contact pins of the motor of the tattoo machine portion to facilitate the transfer of power from the adapter to the motor. The end of the power cable not connected to the connector of the adapter may be connected to a power supply and power may be delivered to the tattoo machine via the adapter. Notably, the printed circuit board may include an internal circuit that ensures that the power delivered to the motor from the adapter has the correct polarity regardless of the input polarity.

In another embodiment, a method for utilizing an adapter with a tattoo machine is disclosed. The method may initially and optionally include removing a wireless battery pack from the tattoo machine. The method may then include aligning a first portion of the adapter with a receptacle of the tattoo machine. Additionally, the method may include inserting the first portion of the adapter axially into the receptacle of the tattoo machine. The method may proceed to include twisting the adapter after the first portion of the adapter is inserted axially into the receptacle until at least one extruded feature of the first portion contacts a ledge of the receptacle of the tattoo machine. Furthermore, the method may include locking, after conducting the twisting, the adapter onto the receptacle of the tattoo machine. In certain embodiments, locking of the adapter onto the receptacle may be based on the at least one extruded feature of the first portion contacting the ledge which may cause an o-ring (or other suitable device) assembled to the adapter to get squeezed between the adapter and the receptacle, thereby generating a pulling force on the at least one extruded feature that causes the adapter to be locked into place with the receptacle. In certain embodiments, when the first portion of the adapter is locked into place with the tattoo machine, plating of a printed circuit board of the adapter may contact pins on a motor assembly of the tattoo machine to facilitate delivery of power to the tattoo machine via the adapter. The method may also include connecting a first end of a power cable to a connector of a second portion of the adapter. The method may also include connecting a second end of the power cable to a power supply for delivering power to the tattoo machine via the adapter. Moreover, the method may include delivering the power to the tattoo machine via the adapter while ensuring a correct polarity for the power is provided to the motor using an internal circuit of the printed circuit board.

According to yet another embodiment, an adapter for use with a tattoo machine is disclosed. The adapter may include a first portion configured to connect to a receptacle of the tattoo machine, and a second portion including a connector configured to connect to a power cable for delivering power to a motor of the tattoo machine when the first portion is connected to the receptacle of the tattoo machine portion. In certain embodiments, the first portion of the adapter may be connected to the receptacle based on at least one extruded feature of the first portion contacting a ledge of the receptacle which causes an o-ring (or other similar device) assembled to the adapter to get squeezed between the adapter and the receptacle, thereby generating a pulling force on the at least one extruded feature that causes the adapter to be connected to the receptacle. An internal circuit of a printed circuit board of the adapter may ensure that the power delivered to the motor has a correct polarity when the first portion is connected to the receptacle—irrespective of the input polarity.

These and other features of the adapter device are described in the following detailed description, drawings, and appended claims.

DETAILED DESCRIPTION OF THE DRAWINGS

An adapter device (e.g., adapter devices 110, 410) for a tattoo machine (e.g. 100, 400) and accompanying methods (e.g. method 1500) for utilizing the adapter device with a tattoo machine are disclosed. In particular, the adapter device may enable a tattoo machine to switch from a fully wireless or other configuration to a wired configuration, such as by removing a wireless battery pack from the tattoo machine and replacing the wireless battery pack with the adapter. In certain embodiments, the adapter may be fitted with a connector, such as, but not limited to, a RCA connector that may couple with a power cable that may be utilized to deliver power to the tattoo machine when the tattoo machine is connected to the adapter and the coupled power cable is connected to a power supply supplying the power. The power supply may be any device may connect to a power source, such as a wall socket or other power source, and which may be utilized to deliver power to the tattoo machine via the adapter. In certain embodiments, the adapter may include a female RCA connector attached on one end of the adapter, and, on the opposite end (or other desired location), the adapter may include a printed circuit board with custom designed plating that is configured to make contact with pins on a motor assembly of the tattoo machine so that power may be transferred to the tattoo machine via the adapter and from the power supply. An internal circuit of the printed circuit board may be configured to ensure that the power delivered to the motor of the tattoo machine via the power cable attached to the female RCA connector always has the correct polarity regardless of the input polarity.

Figure 1A:
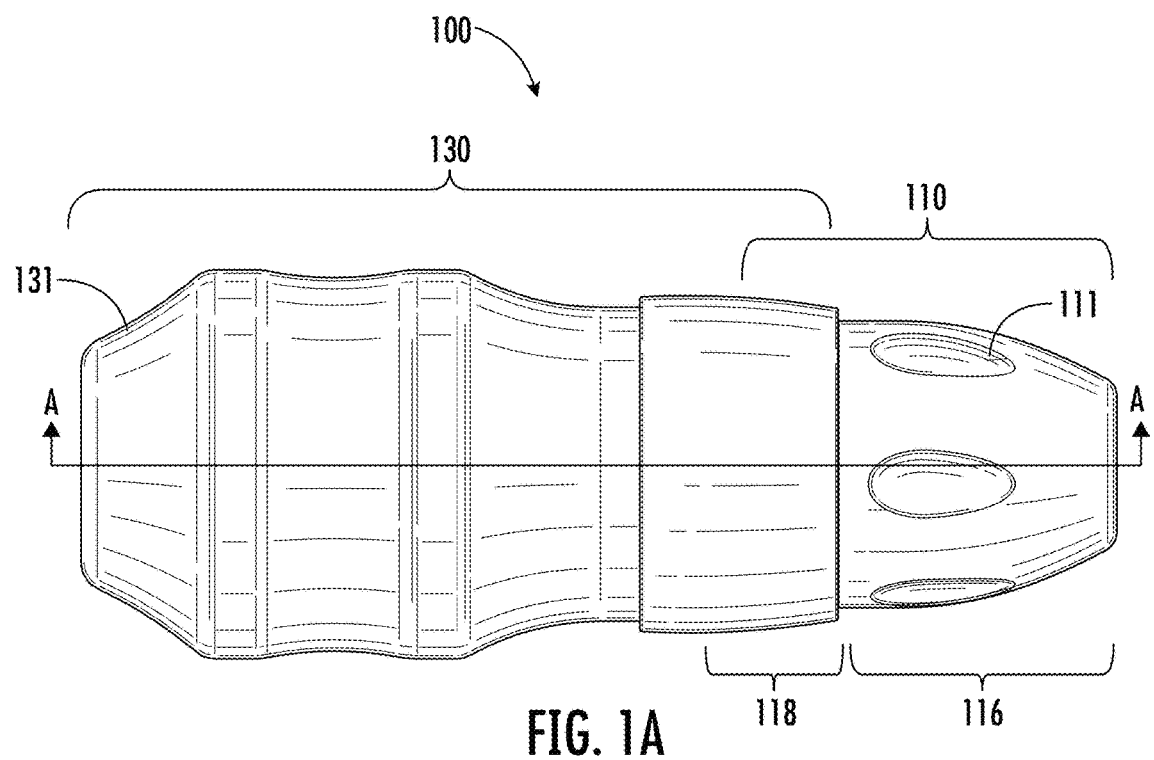
FIGS. 1A-B are schematic diagrams illustrating side and cross-sectional views of an adapter device and tattoo machine combination according to an embodiment of the present disclosure.
Figure 1B:
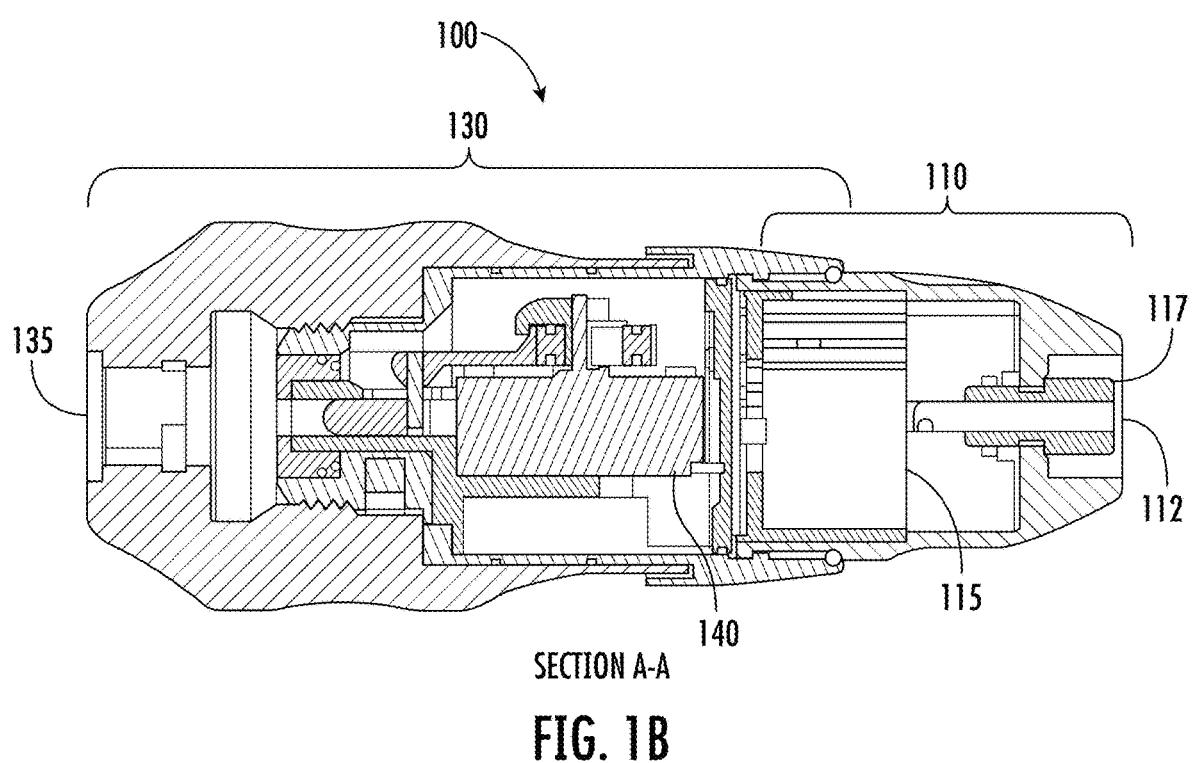
Figure 2A:
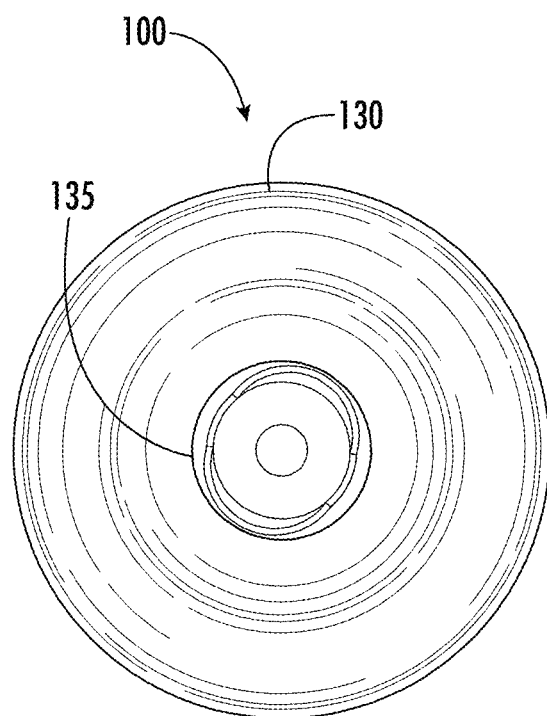
FIGS. 2-A-B are schematic diagrams illustrating front and back views of the adapter device and tattoo machine combination of FIG. 1A.
Figure 2B:
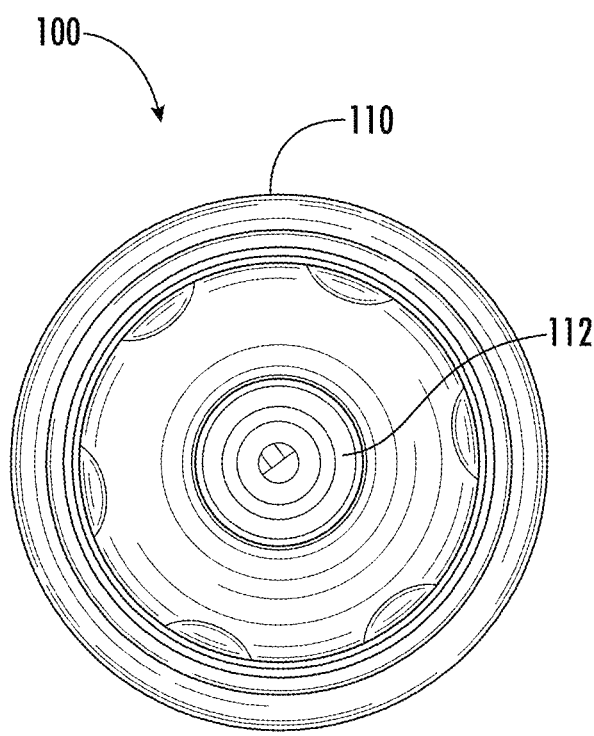
Figure 3A:
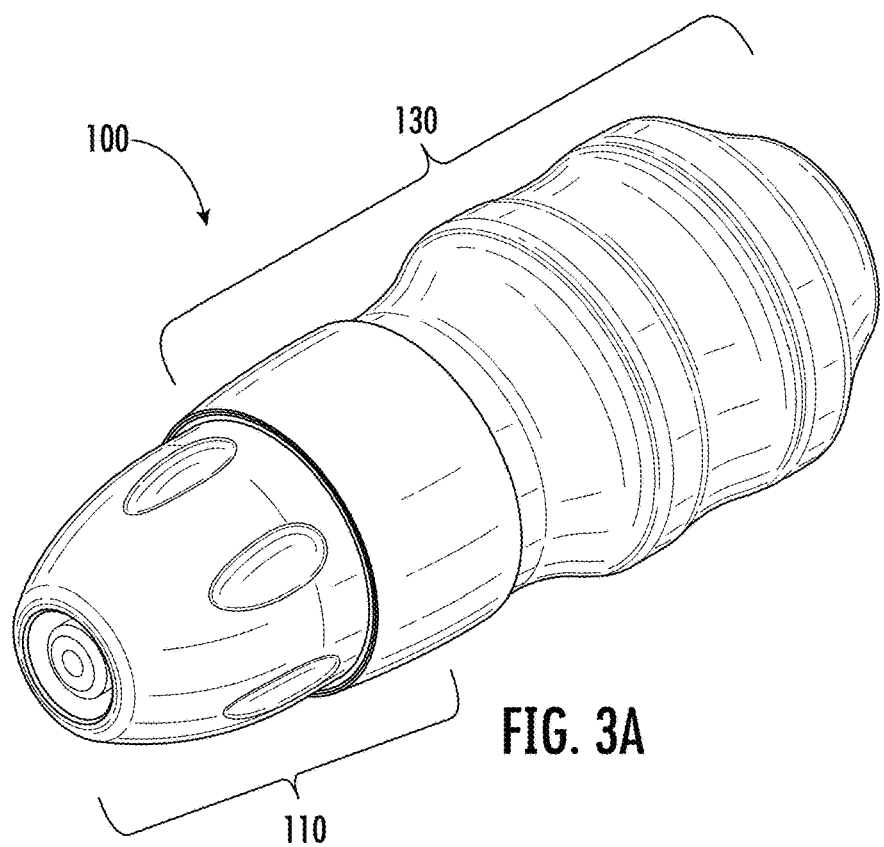
FIGS. 3A-B depict angled forward and back views of the adapter device and tattoo machine combination of FIG. 1A.
Figure 3B:
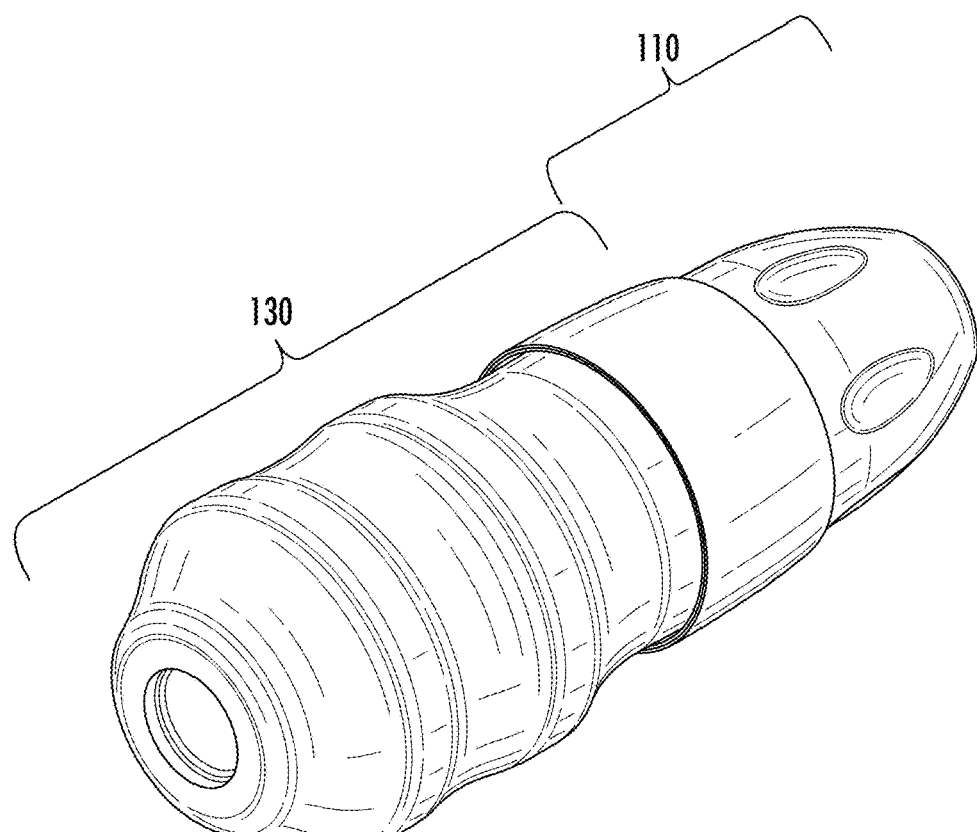
Figure 4A:
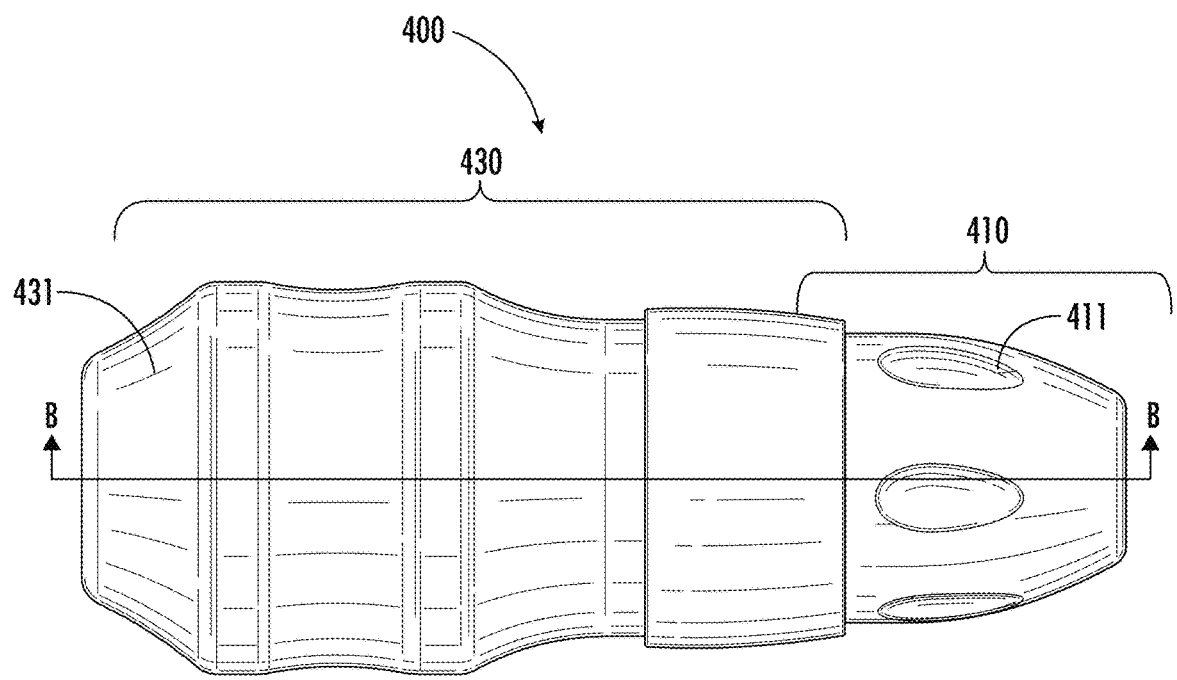
FIGS. 4A-B are schematic diagrams illustrating side and cross-sectional views of another adapter device and tattoo machine combination according to an embodiment of the present disclosure.
Figure 4B:
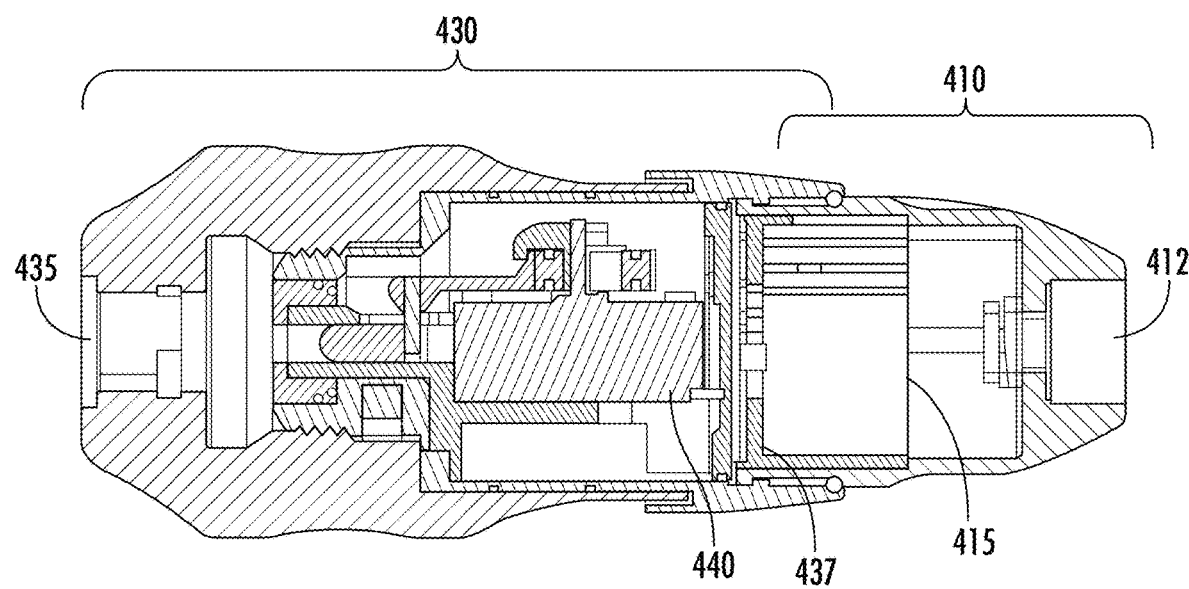
Figure 5A:
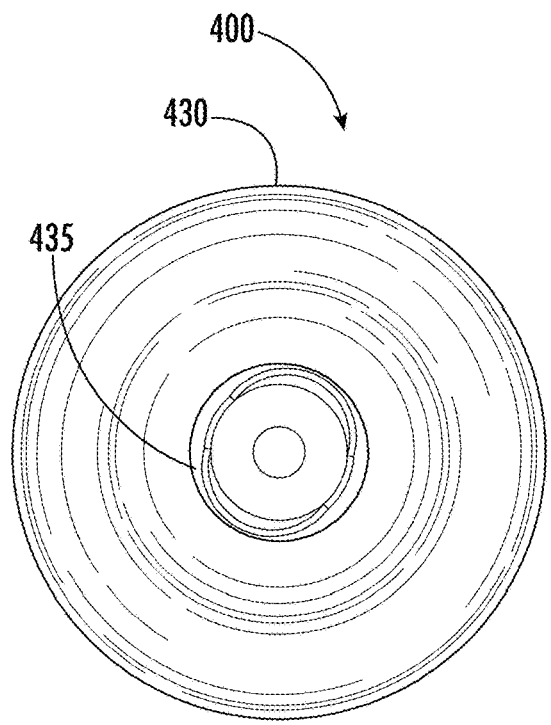
FIGS. 5A-B are schematic diagrams illustrating front and back views of the adapter device and tattoo machine combination of FIG. 4A.
Figure 5B:
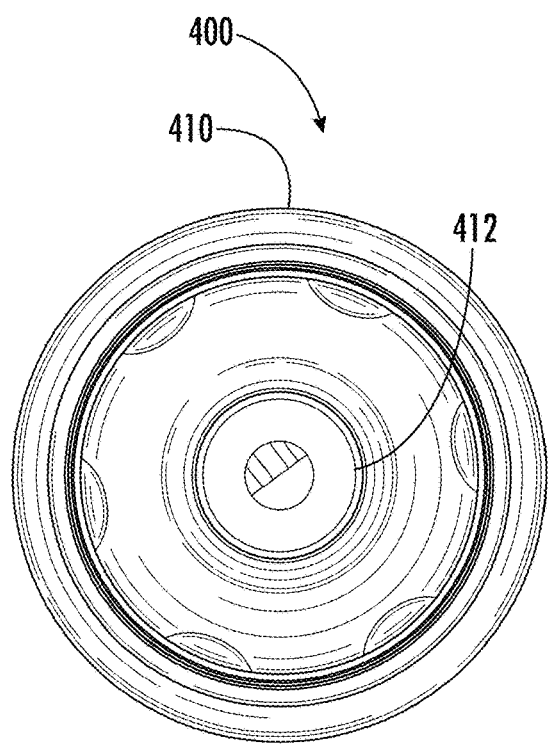
Figure 6A:
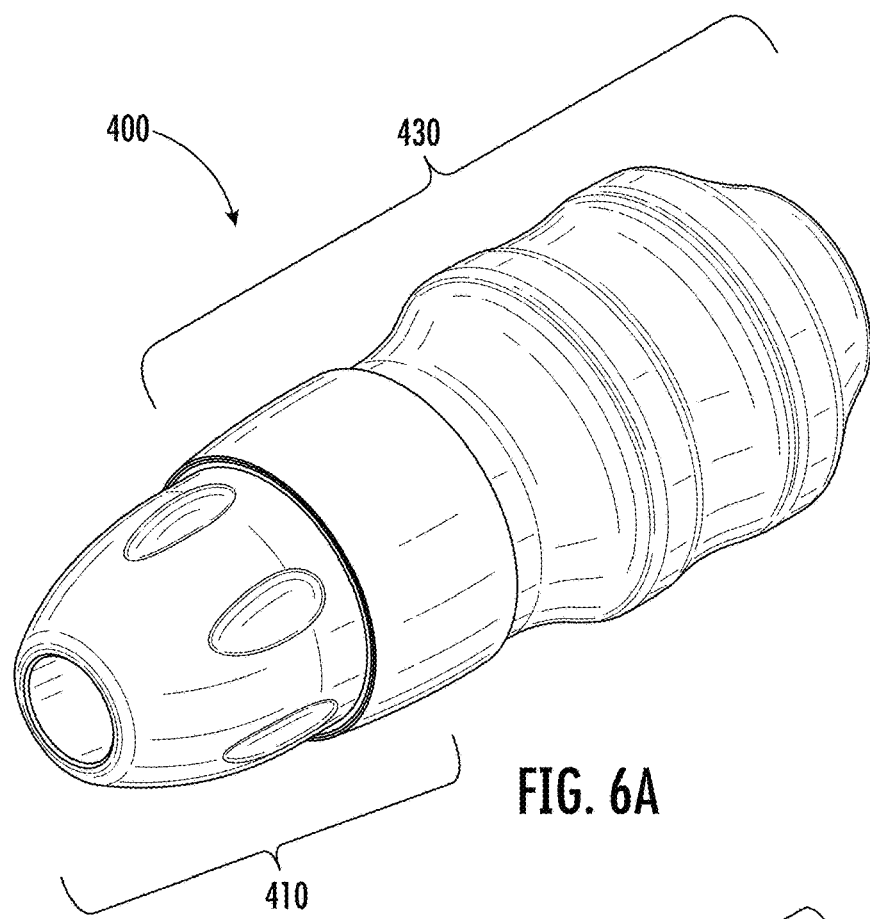
FIGS. 6A-B depict angled forward and back views of the adapter device and tattoo machine combination of FIG. 4A.
Figure 6B:
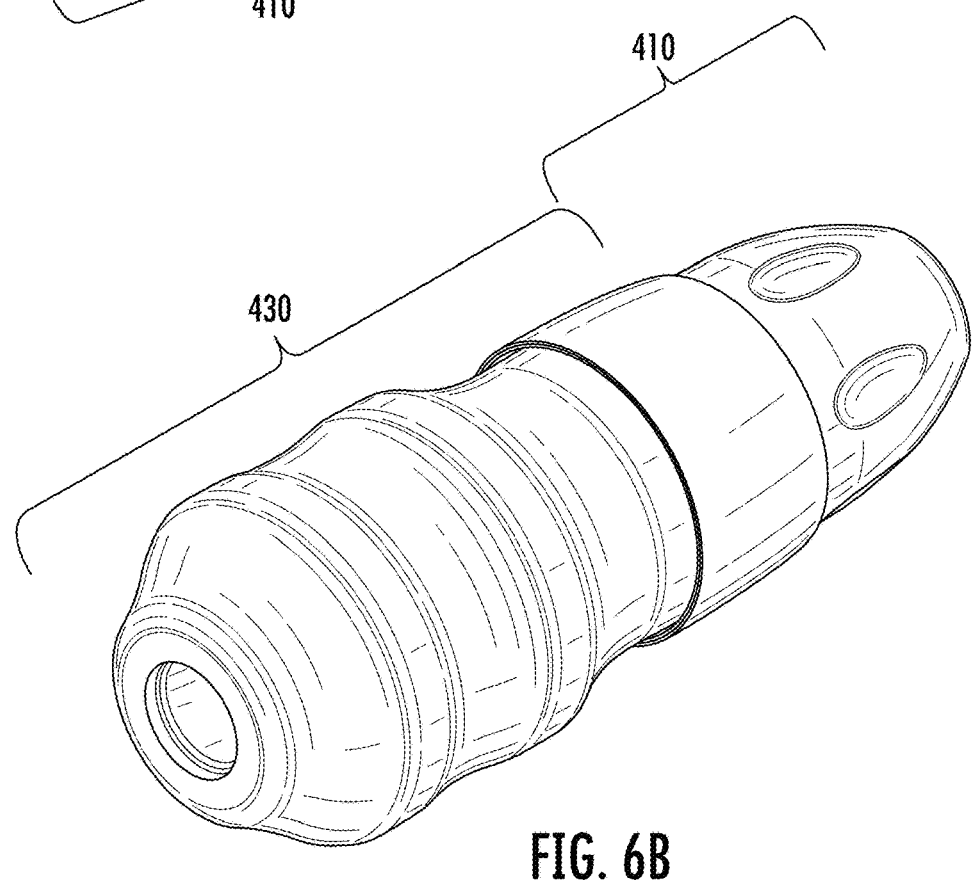
Figure 7:
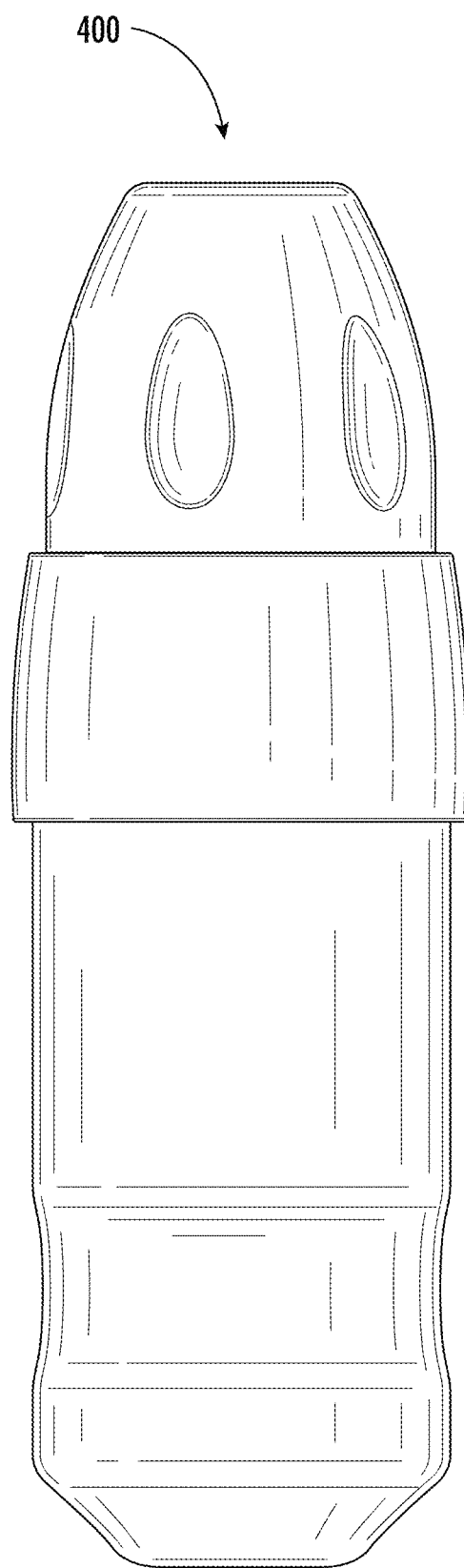
FIG. 7 is a schematic diagram illustrating a vertical view of the adapter and tattoo machine combination of FIG. 4A.
Figure 8:
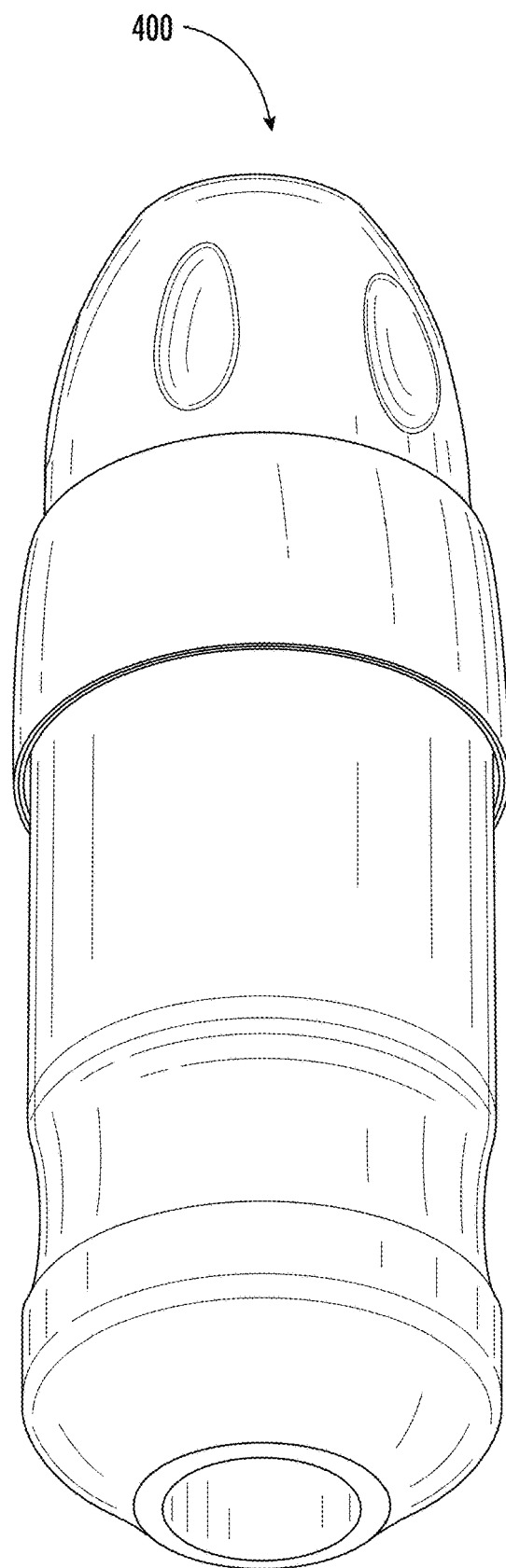
FIG. 8 is a schematic diagram illustrating an angled view of the adapter and tattoo machine combination of FIG. 4A.
Figure 9A:
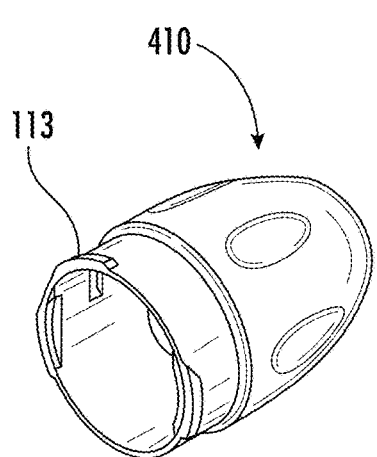
FIGS. 9A, 9B, 9C, 9D, 9E, and 9-F are schematic diagrams illustrating various views of an adapter for use with a tattoo machine according to an embodiment of the present disclosure.
Figure 9B:
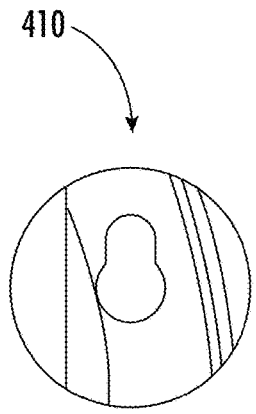
Figure 9C:
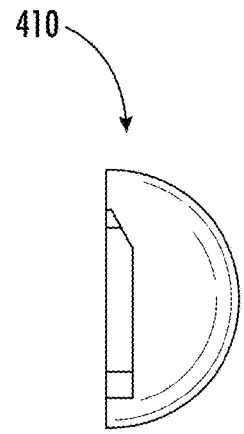
Figure 9D:
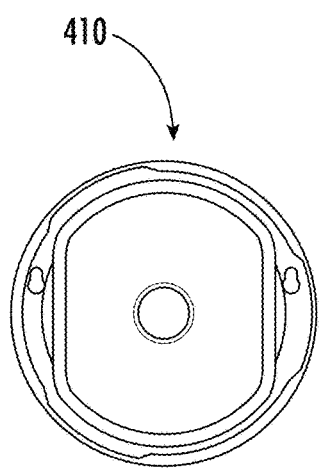
Figure 9E:
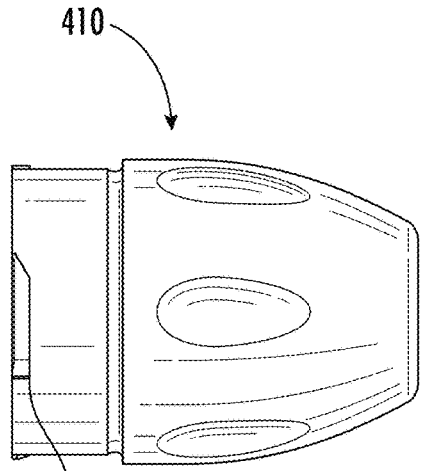
Figure 9F:
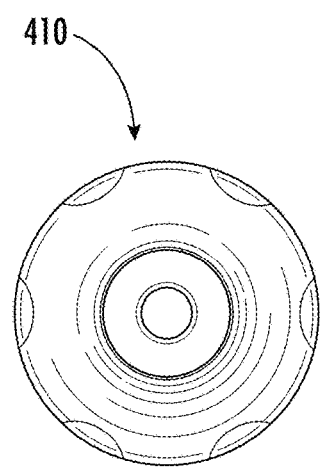
Figure 10A:
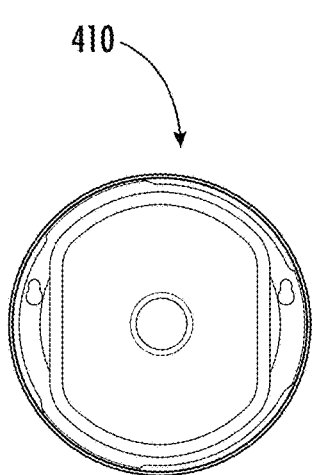
FIGS. 10A, 10B, 10C, 10D, 10E, 10-F are schematic diagrams illustrating various views of an adapter for use with a tattoo machine according to an embodiment of the present disclosure.
Figure 10B:
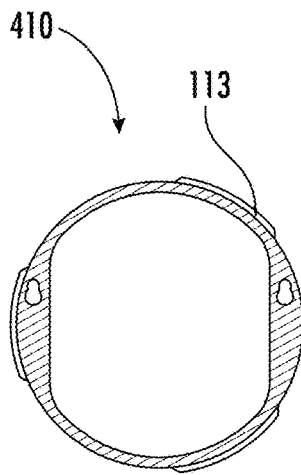
Figure 10C:
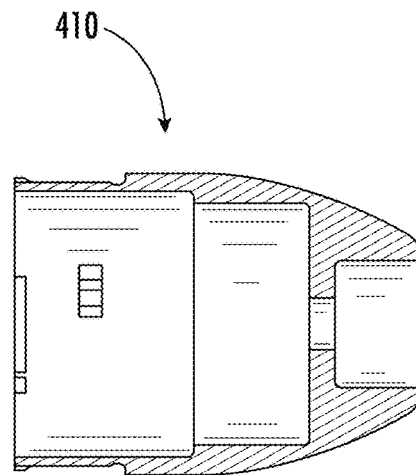
Figure 10D:
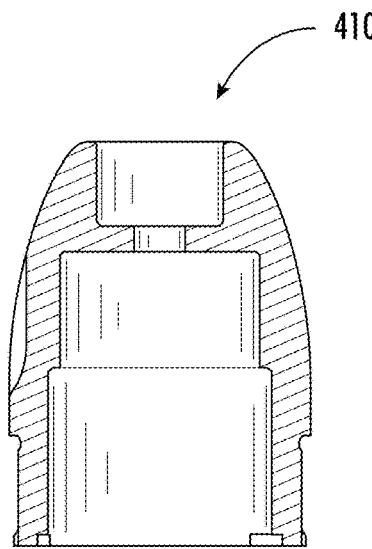
Figure 10E:
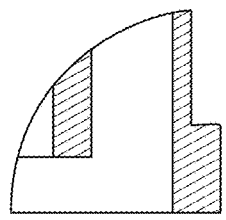
Figure 10F:
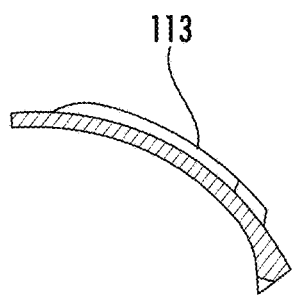
Figure 11:
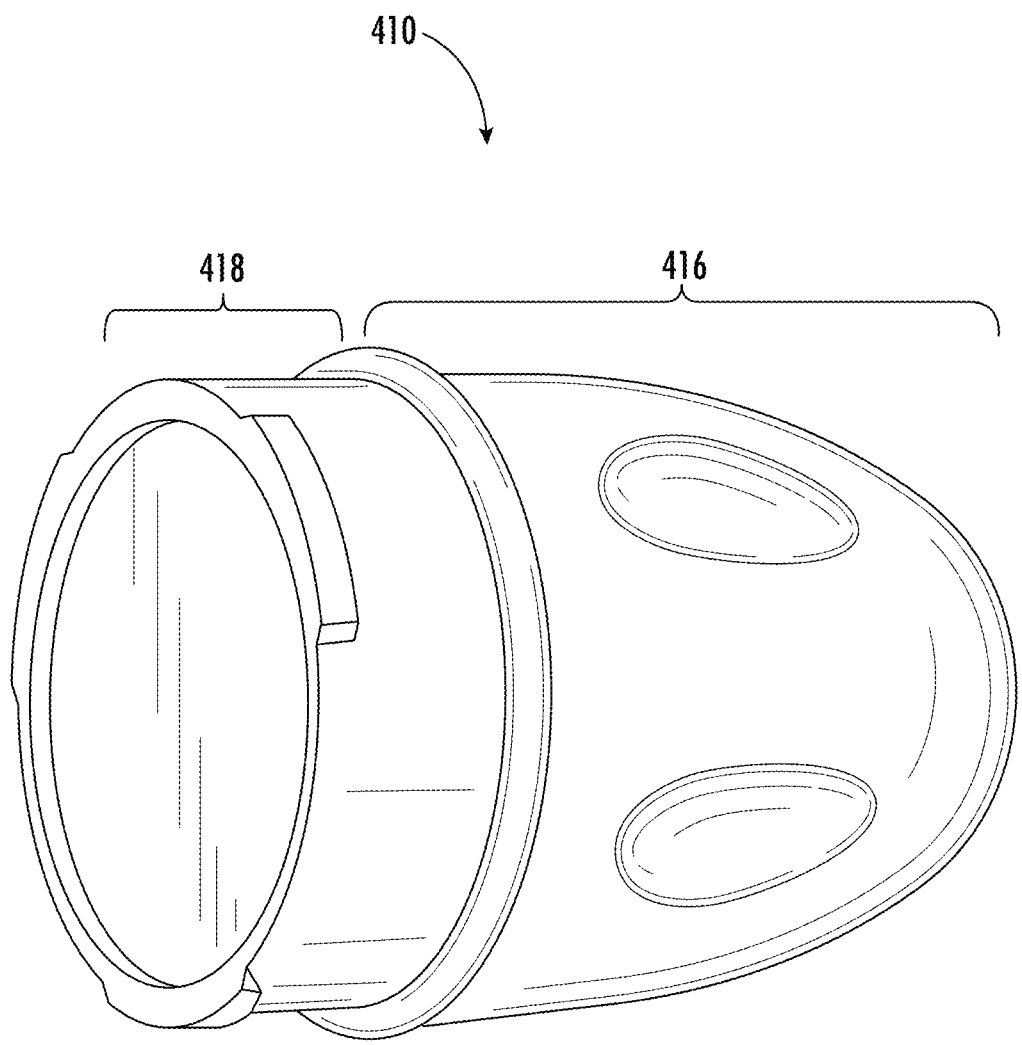
FIG. 11 is a schematic diagram illustrating a side view of an adapter for use with a tattoo machine according to an embodiment of the present disclosure.
Figure 12:
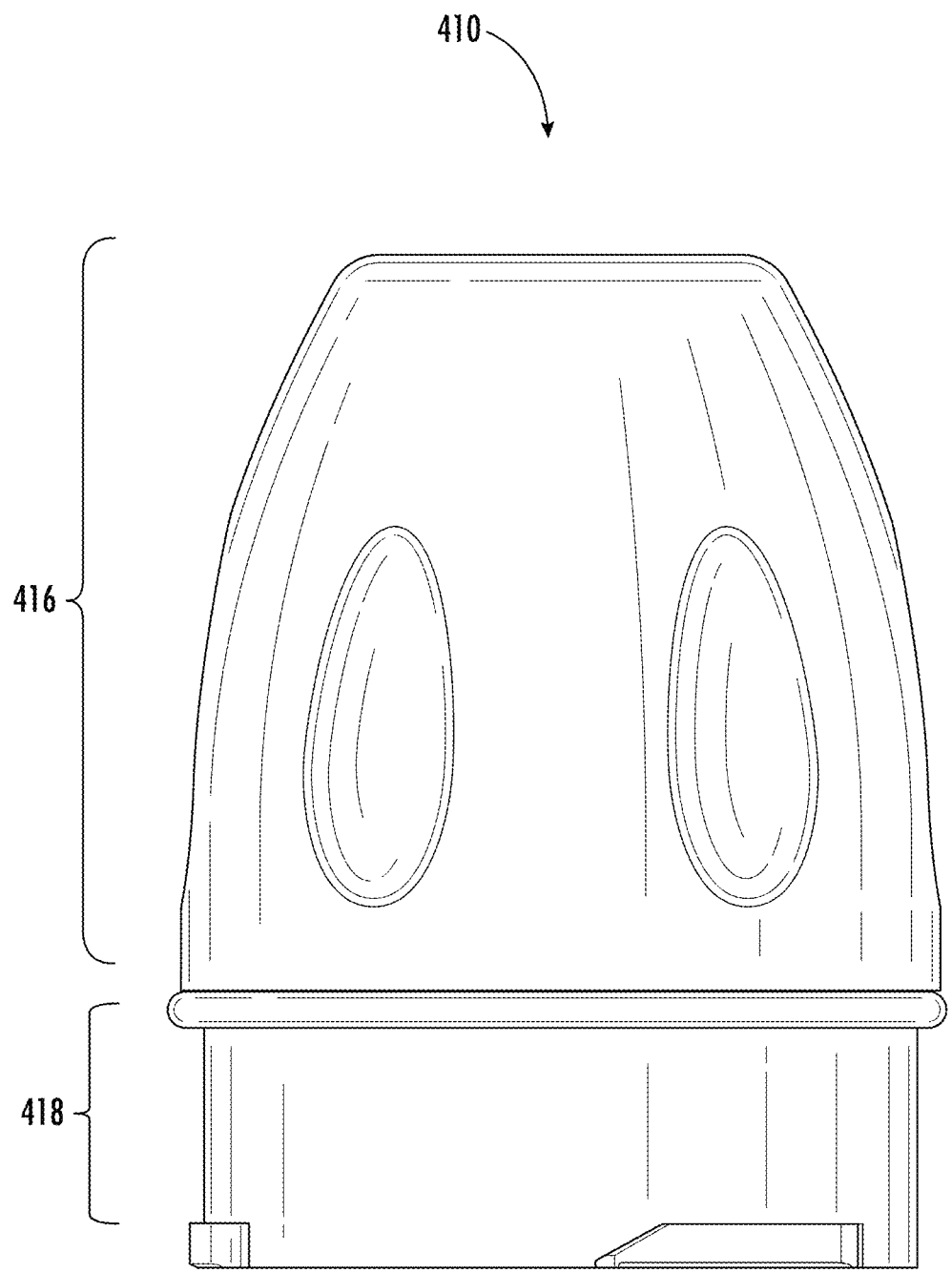
FIG. 12 is a schematic diagram illustrating a vertical view of an adapter for use with a tattoo machine according to an embodiment of the present disclosure.
Figure 13A:
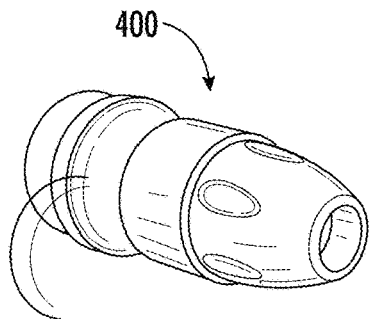
FIGS. 13A, 13B, 13C, 13D, 13E, 13F, 13G, 13H, 13I, and 13-J are schematic diagrams illustrating various views of various embodiments of an adapter and tattoo machine combination according to embodiments of the present disclosure.
Figure 13B:
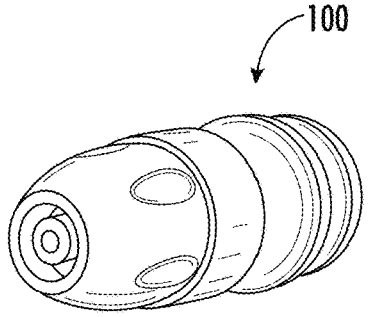
Figure 13C:
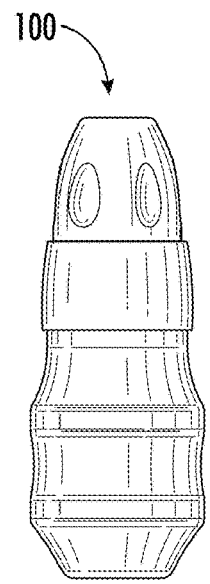
Figure 13D:
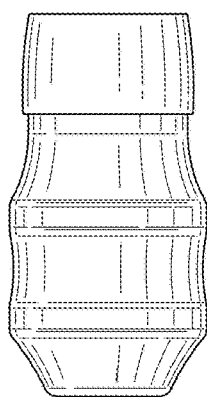
Figure 13E:
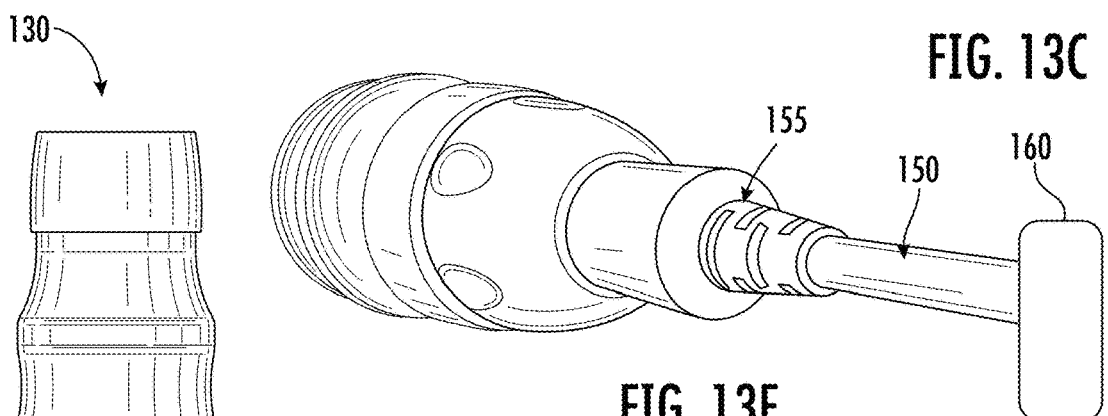
Figure 13G:
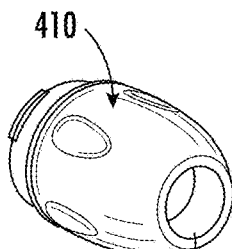
Figure 13I:
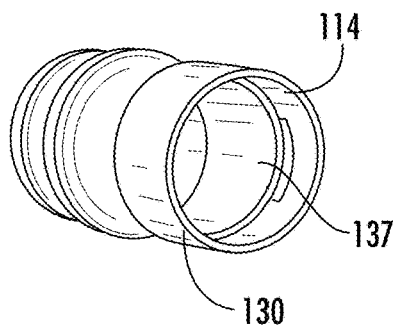
Figure 13F:
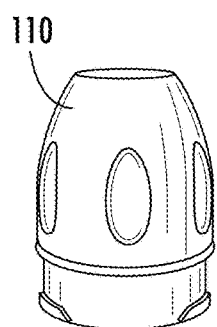
Figure 13H:
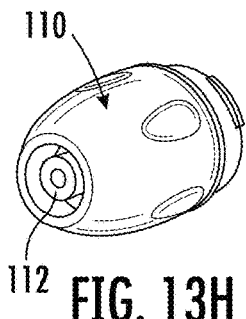
Figure 13J:
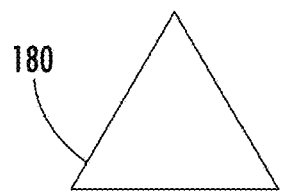

As shown in FIG. 1A-B and referring also to FIGS. 2A-2B-3A-B, embodiments of a tattoo machine 100 including a tattoo machine portion 130 and an adapter 110 is disclosed. The tattoo machine 100 may be utilized to apply tattoo ink onto the skin of a tattoo recipient, such as a person. In certain embodiments, the tattoo machine portion 130 of the tattoo machine 100 may include a grip 131 that a tattoo artist may grip while utilizing the tattoo machine 100. Additionally, the tattoo machine portion 130 may include a motor 140 that may be utilized to power and actuate the various components of the tattoo machine 100. The tattoo machine portion 130 may also include a receptacle 135, which may be configured to receive a needle cartridge containing a needle(s) that may be utilized to deliver ink onto the skin of a tattoo recipient. Furthermore, the tattoo machine portion 130 may also include another receptacle 137 (see FIGS. 13A, 13B, 13C, 13D, 13E, 13F, 13G, 13H, 13I, and 13J) that may be configured to couple with the adapter 110. The motor 140 of the tattoo machine portion 130 may be utilized to drive the needle so that the ink may be applied onto the skin of the tattoo recipient. In certain embodiments, the adapter 110 of the tattoo machine 100 may serve as a housing that may include a connector 112 and a printed circuit board 115. In certain embodiments, the connector 112 may be a female RCA connector, a ¼ Jack connector, a male RCA connector, a 9V connector, any type of connector, or a combination thereof. In this example, the connector 112 may be a connector that enables a RCA version of the cable 150 to couple to the connector 112. The connector 112 may include a cylindrical shaped structure 117 (or other shape) that may be configured to couple with an end of a power cable 150, which may, for example, include an RCA or other plug. The connector 112 may couple and connect with the power cable 150 (see FIGS. 13A, 13B, 13C, 13D, 13E, 13F, 13G, 13H, 13I, and 13J), which may connect with a power supply 160 that may deliver power to the adapter 110 via the power cable 150. In certain embodiments, the adapter 110 may include one or more grooves 111 on a second portion 116, which may enable a user to securely grab onto the adapter 110, such as when connecting the adapter 110 to the tattoo machine portion 130. In certain embodiments, the printed circuit board 115 of the adapter 110 may be utilized to transfer power from a connected power cable 150 when the adapter 110 is connected to the tattoo machine portion 130 to the motor 140 of the tattoo machine 100. In certain embodiments, the printed circuit board 115 may include an internal circuit that may be utilized to ensure that the power delivered to the motor 140 of the tattoo machine portion 130 has the correct polarity irrespective of the input polarity. In certain embodiments, the printed circuit board 115 of the adapter 110 may include a custom-designed plating that makes contact with pins on the motor 140 when the adapter 110 is connected to the tattoo machine portion 130.

In order to connect the adapter 110 to the tattoo machine portion 130, a user may align a first portion 118 of the adapter 110 with the receptacle 137 of a tattoo machine portion 130. The user may then insert the first portion 118 of the adapter 110 axially into the receptacle 137. Once inserted, the user may twist the adapter, such as in a clockwise motion (or other suitable and/or desired motion). The twisting motion may cause one or more extruded features 113 (e.g. three extruded features or other number of extruded features) of the first portion 118 of the adapter 110 to contact one or more ledges 114 of the tattoo machine portion 130. Once contact between the one or more ledges 114 and the one or more extruded features 113 is made, an o-ring (or other similar device) of the adapter 110 may be squeezed between the adapter 110 and the body of the tattoo machine portion 130 (via the receptacle 137) such that a pulling force may be generated on each of the extruded features 113 to cause the adapter 110 to lock into place with the receptacle 137 of the tattoo machine portion 130. The user may then connect one end of the power cable 150 to the power supply 160 and the other end 155 to the connector 112. The power supply 160 may then provide power to the adapter 110, which may then deliver the power to the motor 140 of the tattoo machine portion 130 so that the tattoo artist may utilize the tattoo machine 100 to apply ink to a tattoo recipient.

In another embodiment, as shown in FIGS. 4-12, another adapter 410 may be utilized with a tattoo machine 400 and a tattoo machine portion 430. Much like tattoo machine 100, the tattoo machine 400 may be utilized to apply tattoo ink onto the skin of a tattoo recipient. In certain embodiments, the tattoo machine 400, the tattoo machine portion 430, and the adapter 410 may include some or all of the same components as found in tattoo machine 100, tattoo machine portion 130, and/or adapter 110. The tattoo machine portion 430 of the tattoo machine 400 may include a grip 431 that a tattoo artist may grab onto while utilizing the tattoo machine 400. Additionally, the tattoo machine portion 430 may include a motor 440 that may be utilized to power and actuate the various components of the tattoo machine 400. The tattoo machine portion 430 may also include a receptacle 435, which may be configured to receive a needle cartridge containing any number of needles that may be utilized to deliver ink onto the skin of a user. Furthermore, the tattoo machine portion 430 may also include another receptacle 437 (similar to receptacle 137) that may be configured to couple with the adapter 410. The motor 440 of the tattoo machine portion 430 may be utilized to drive the needle so that the ink may be applied onto the skin of the tattoo recipient. In certain embodiments, the adapter 410 of the tattoo machine 400 may serve as a housing that may include a connector 412 and a printed circuit board 415. The housing may be made of any suitable material including, but not limited to, aluminum, titanium, plastic (e.g. POM, ABS, etc.), any material, or any combination thereof. In certain embodiments, the connector 412 may be a female RCA connector, a ¼ Jack connector, a male RCA connector, a 9V connector, any type of connector, or a combination thereof. In certain embodiments, instead of having the cylindrical shaped structure 117 (or other shape) of adapter 110, the adapter 410 may have a configuration to receive other types of plugs designs for different power cables 150. The configuration may be a receptacle as shown in FIG. 4A-B and/or any type of structure that can accommodate any type of plug design of a power cable. The connector 412 may couple and connect with the power cable 150 (see FIGS. 13A, 13B, 13C, 13D, 13E, 13F, 13G, 13H, 13I, and 13J), which may connect with a power supply 160 that may deliver power to the adapter 410 via the power cable 150. In certain embodiments, the adapter 410 may include one or more grooves 411, which may enable a user to securely grab onto the adapter 410, such as when connecting the adapter 410 to the tattoo machine portion 430. In certain embodiments, the printed circuit board 415 of the adapter 410 may be utilized to transfer power from a connected power cable 150 when the adapter 410 is connected to the tattoo machine portion 430 to the motor 440 of the tattoo machine 400. In certain embodiments, the printed circuit board 415 may include an internal circuit that may be utilized to ensure that the power delivered to the motor 440 of the tattoo machine portion 430 has the correct polarity, irrespective of the input polarity. In certain embodiments, the printed circuit board 415 of the adapter 410 may include a custom-designed plating that makes contact with pins on the motor 440 when the adapter 410 is connected to the tattoo machine portion 430.

Connecting the adapter 410 to the tattoo machine portion 430 may be similar to connecting adapter 110 to the tattoo machine portion 130. In particular, in order to connect the adapter 410 to the tattoo machine portion 430, a user may align a first portion 418 of the adapter 410 with the receptacle 437 of a tattoo machine portion 430. The user may then insert the first portion 418 of the adapter 410 axially into the receptacle 437. Once inserted, the user may twist the adapter, such as in a clockwise motion (or other suitable and/or desired motion). The twisting motion may cause one or more extruded features 113 of the first portion 418 of the adapter 410 to contact one or more ledges 114 of the tattoo machine portion 430. Once contact between the one or more ledges 114 and the one or more extruded features 113 is made, an o-ring (or other similar device) of the adapter 410 may be squeezed between the adapter 410 and the body of the tattoo machine portion 430 (via the receptacle 437) such that a pulling force may be generated on each of the extruded features 113 to cause the adapter 410 to lock into place with the receptacle 437 of the tattoo machine portion 430. The user may then connect one end of the power cable 150 to the power supply 160 and the other end 155 to the connector 412. The power supply 160 may then provide power to the adapter 410, which may then deliver the power to the motor 440 of the tattoo machine portion 430 so that the tattoo artist may utilize the tattoo machine 400 to apply ink to a tattoo recipient.

Figure 14:
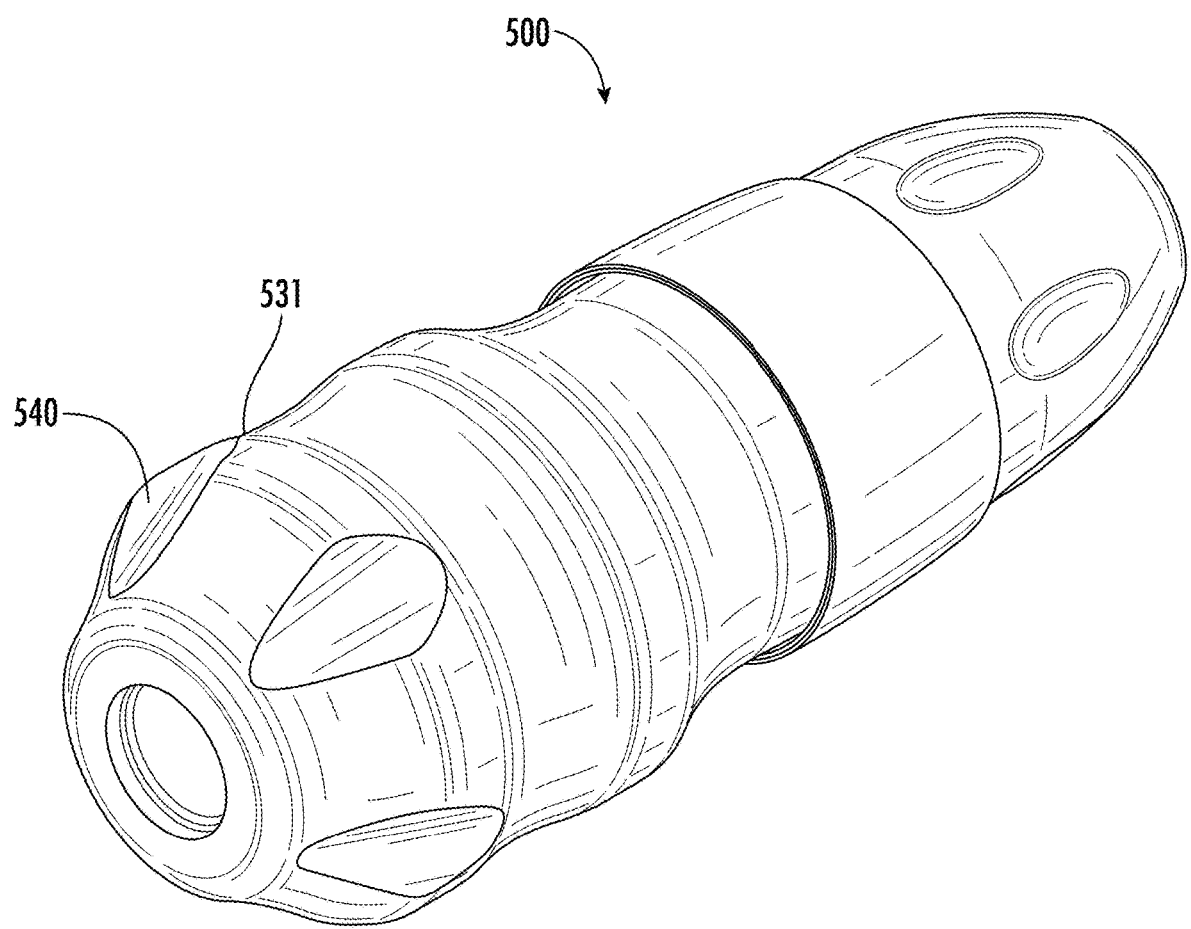
FIG. 14 is a schematic diagram illustrating a perspective view of another adapter and tattoo machine combination according to an embodiment of the present disclosure.

Referring now also to FIG. 14, another embodiment of a tattoo machine 500 is schematically illustrated. The tattoo machine 500 may include any of the components of the tattoo machines 100, 400, along with any other desired components. In certain embodiments, the tattoo machine 500 may include a specialized grip 531, which may include one or more grooves 540 (or dimples, notches, indentations, or structures). The grooves 540 may be utilized to enhance a user's grip onto the grip 531, reduce the weight of the grip 531 and/or tattoo machine 500, and tattoo machine ergonomics.

Although FIGS. 1A-15 illustrates specific example configurations of the various adapters 110, 410, tattoo machine portions 130, 140, and tattoo machines 100, 400, these devices may include any configuration of the components, which may include using a greater or lesser number of the components. For example, the adapters 110, 410, the tattoo machine portions 130, 140, the tattoo machines 100, 400, and/or any of the other components shown in FIGS. 1A-14 may include any number extruded features 113, ledges 114, receptacles 137, 437, connectors 112, 412, grips 131, 431, receptacle 135, 435, connectors 112, 412, motors 140, 440, printed circuit boards 115, 415, and/or any number of other components. Additionally, components of tattoo machine 100 may be utilized with components of tattoo machine 400 and vice versa. Additionally, the power cable 150 may be configured to connect with any type of power source, such as via a port/socket of the footswitch 180, which may be connected to another power source. A user may use the footswitch 180 to control the voltage delivered to the tattoo machines 100, 400, such as by depressing pedals/buttons/controls on the footswitch 180 with the user's feet. Other intermediary devices instead of a footswitch 180 may also be utilized to deliver power to the tattoo machines 100, 400.

Figure 15:
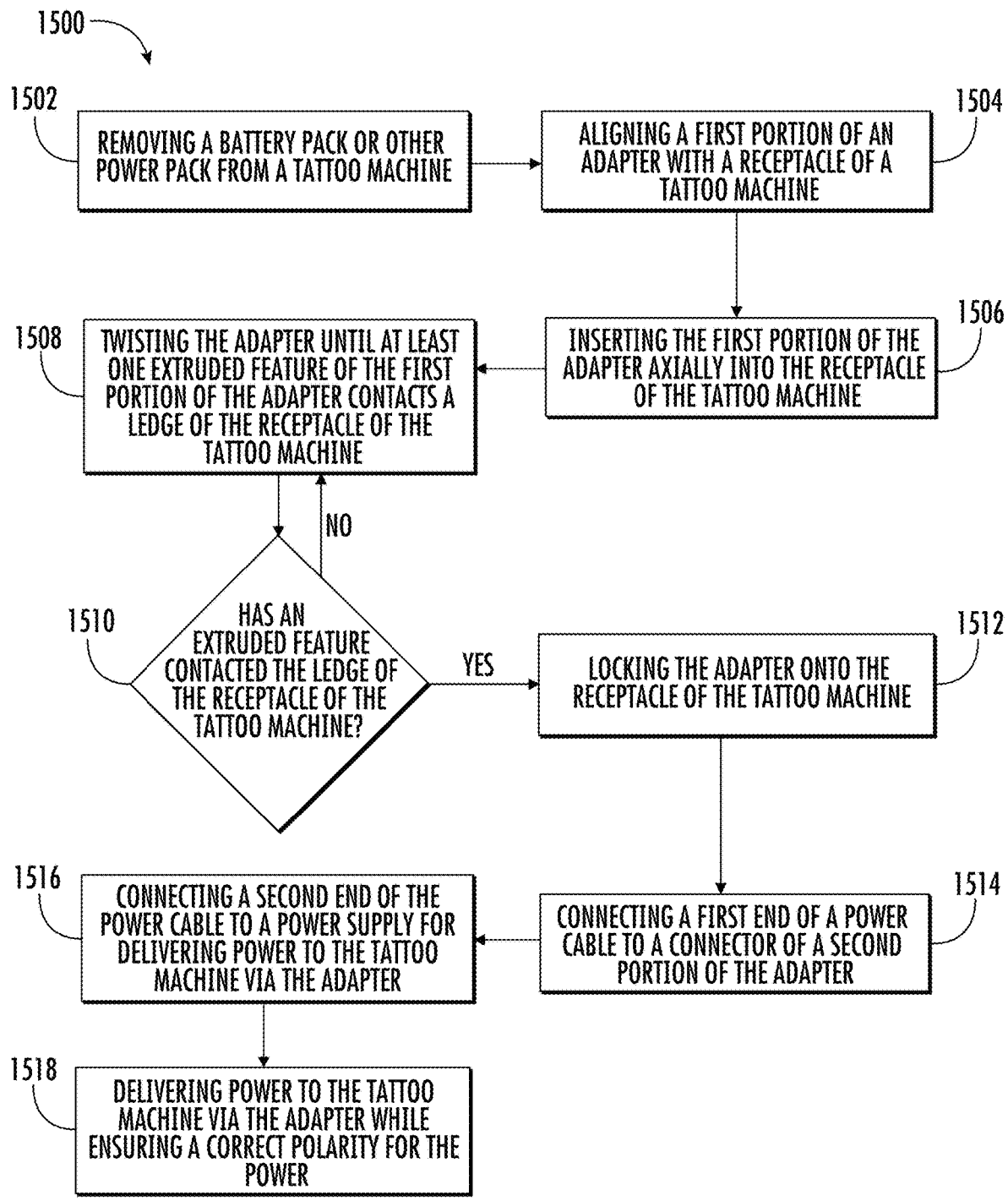
FIG. 15 is a flow diagram illustrating a sample method for utilizing an adapter with a tattoo machine according to an embodiment of the present disclosure.

Notably, as shown in FIG. 15, an exemplary method 1500 for utilizing an adapter (e.g. adapter 110, 410) with a tattoo machine (e.g. 100, 400) is schematically illustrated. The method 1500 may include, optionally, at step 1502, removing a battery pack, such as a wireless battery pack from a tattoo machine, such as tattoo machine 100 and/or 400. At step 1504, the method 1500 may include aligning a first portion of the adapter with a receptacle of the tattoo machine. The method 1500 may proceed to step 1506, which may include inserting the first portion of the adapter axially into the receptable of the tattoo machine. At step 1508, the method 1500 may include twisting the adapter until at least one extruded feature of the first portion of the adapter contacts a ledge of the tattoo machine. At step 1510, the method 1500 may include determining if the at least one extruded feature has contacted the ledge of the receptacle of the tattoo machine. If not, the method 1500 may revert back to step 1508 until the at least one extruded feature has contacted the ledge of the tattoo machine. If so, the method 1500 may proceed to step 1512, which may include locking the adapter onto the receptacle of the tattoo machine so that the adapter and the tattoo machine are combined. At step 1514, the method 1500 may include connecting a first end of a power cable to a connector of the adapter (e.g. second portion 416). At step 1516, the method 1500 may include connecting a second end of the power cable to a power supply for delivering power to the tattoo machine via the adapter. At step 1518, the method 1400 may include delivering the power to the tattoo machine via the adapter while ensuring a correct polarity for the power. A user may then use the operable tattoo machine to apply ink to the skin of a user. Notably, the method 1500 may further incorporate any of the features and functionality described herein.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A tattoo system comprising:
    a tattoo tool, wherein the tattoo tool comprises:
        an elongated tattoo tool housing that comprises a working end and a power interface opposite the working end;
        a receptacle opening defined at the working end of the elongated tattoo tool housing and configured to receive a needle cartridge;
        a plurality of grooves arranged on an outside surface of the working end of the tattoo tool housing;
        a motor disposed within the elongated tattoo tool housing and configured to drive a needle of the needle cartridge, wherein the motor comprises one or more electrical terminals configured to communicate power to the motor; and
    an adapter configured to be releasably coupled to the tattoo tool, wherein the adapter comprises:
        an adapter housing that comprises a tool interface and a power receiving section;
        a plurality of grooves arranged on an outside surface of the adapter housing;
        a printed circuit board configured to transfer power received via a power cable to the motor of the tattoo tool, wherein the printed circuit board is housed in the adapter housing such that the printed circuit board remains part of the adapter when the adapter is released from the tattoo tool; and
        an RCA connector disposed at the power receiving section of the adapter housing,
        wherein the power interface of the tattoo tool defines a cylindrical feature, and the tool interface of the adapter defines a complementary cylindrical feature, wherein when the adapter is coupled to the tattoo tool, the respective cylindrical features are configured to overlap one another to facilitate releasably securing the adapter to the tattoo tool and transferring power received via the RCA connector to the motor via the electrical terminals of the motor.

2. The tattoo system according to claim 1, wherein the adapter is at least partially rotatable about a longitudinal axis of the tattoo tool while the respective cylindrical features overlap one another.

3. The tattoo system according to claim 1, wherein the power cable is configured to be releasably coupled to the RCA connector.

4. The tattoo system according to claim 1, wherein the printed circuit board comprises contact pads configured to electrically coupled to the one or more electrical terminals of a battery.

5. The tattoo system according to claim 1, wherein the printed circuit board comprises circuitry configured to ensure that the power transferred to the motor has a correct polarity irrespective of input polarity.

6. The tattoo system according to claim 1, wherein the power interface of the adapter has a diameter less than a diameter of a power interface of the tattoo tool.

7. The tattoo system according to claim 1, wherein the tool interface of the adapter comprises an o-ring.

8. The tattoo system according to claim 1, wherein the adapter housing is made of aluminum, titanium, plastic, or a combination thereof.

9. The tattoo system according to claim 1, further comprising a power pack configured to be releasably coupled to the tattoo tool, wherein the power pack comprises:
    a power pack housing that comprises a tool interface;
    a plurality of grooves arranged on an outside surface of the power pack housing;
    a rechargeable battery disposed within the power pack housing,
    wherein the tool interface of the power pack defines a cylindrical feature that complements the cylindrical feature of the power interface of the tattoo tool, wherein when the power pack is coupled to the tattoo tool, the respective cylindrical features are configured to overlap one another to facilitate releasably securing the power pack to the tattoo tool and transferring energy stored in the rechargeable battery to the motor via the electrical terminals of the motor.

10. A tattoo system comprising:
    a tattoo tool, wherein the tattoo tool comprises:
        an elongated tattoo tool housing that comprises a working end and a power interface opposite the working end;
        a receptacle opening defined at the working end of the elongated tattoo tool housing and configured to receive a needle cartridge;
        a motor disposed within the elongated tattoo tool housing and configured to drive a needle of the needle cartridge, wherein the motor comprises one or more electrical terminals configured to communicate power to the motor; and
    an adapter configured to be releasably coupled to the tattoo tool, wherein the adapter comprises:
        an adapter housing that comprises a tool interface and a power receiving section;
        a printed circuit board configured to transfer power received via a power cable to the motor of the tattoo tool, wherein the printed circuit board is housed in the adapter housing such that the printed circuit board remains part of the adapter when the adapter is released from the tattoo tool; and
        an RCA connector disposed at the power receiving section of the adapter housing,
        wherein the power interface of the tattoo tool defines a cylindrical feature, and the tool interface of the adapter defines a complementary cylindrical feature, wherein when the adapter is coupled to the tattoo tool, the respective cylindrical features are configured to overlap one another to facilitate releasably securing the adapter to the tattoo tool and transferring power received via the RCA connector to the motor via the electrical terminals of the motor.

11. The tattoo system according to claim 10, wherein the adapter is at least partially rotatable about a longitudinal axis of the tattoo tool while the respective cylindrical features overlap one another.

12. The tattoo system according to claim 10, wherein the power cable is configured to be releasably coupled to the RCA connector.

13. The tattoo system according to claim 10, wherein the printed circuit board comprises contact pads configured to electrically coupled to the one or more electrical terminals of a battery.

14. The tattoo system according to claim 10, wherein the printed circuit board comprises circuitry configured to ensure that the power transferred to the motor has a correct polarity irrespective of input polarity.

15. The tattoo system according to claim 10, wherein the power interface of the adapter has a diameter less than a diameter of a power interface of the tattoo tool.

16. The tattoo system according to claim 10, wherein the tool interface of the adapter comprises an o-ring.

17. The tattoo system according to claim 10, wherein the adapter housing is made of aluminum, titanium, plastic, or a combination thereof.

18. The tattoo system according to claim 10, further comprising a power pack configured to be releasably coupled to the tattoo tool, wherein the power pack comprises:
   a power pack housing that comprises a tool interface;
   a plurality of grooves arranged on an outside surface of the power pack housing;
   a rechargeable battery disposed within the power pack housing,
   wherein the tool interface of the power pack defines a cylindrical feature that complements the cylindrical feature of the power interface of the tattoo tool, wherein when the power pack is coupled to the tattoo tool, the respective cylindrical features are configured to overlap one another to facilitate releasably securing the power pack to the tattoo tool and transferring energy stored in the rechargeable battery to the motor via the electrical terminals of the motor.

* * * * *